United States Patent [19]

Boumendjel et al.

[11] Patent Number: 5,430,169
[45] Date of Patent: Jul. 4, 1995

[54] METHOD FOR PREPARATION OF SPHINGOID BASES

[75] Inventors: Ahcene Boumendjel, Bethesda; Stephen P. F. Miller, Rockville, both of Md.

[73] Assignee: The United States of America represented by the Department of Health and Human Services, Washington, D.C.

[21] Appl. No.: 195,815

[22] Filed: Feb. 14, 1994

[51] Int. Cl.$^6$ ............................................. C07F 9/09
[52] U.S. Cl. ................................. 558/169; 558/119; 558/122; 558/131
[58] Field of Search ............................ 558/119, 169

[56] References Cited

U.S. PATENT DOCUMENTS 4,782,019 11/1988 Kokusho et al. .
5,256,641 10/1993 Yatvin et al. .
5,260,288 11/1993 Igarashi et al. .

OTHER PUBLICATIONS

Bannwarth et al., "A Simple And Effective Chemical Phosphorylation Procedure for Biomolecules," Helivetica Chemica Acta (70), pp. 175–186 (1987).
Garner et al., "The Synthesis and Configurational Stability of Differentially Protected β-Hydroxy-a-amino Aldehydes", (52), pp. 2361–2364 (1987).
Ghosh, T. K. et al., "Intracellular Calcium Release Mediated by Sphingosine Derivatres Generated in Cells", Science, 248, 1653–1656 (1990).
Hannun, Y. A. et al., "Functions of Sphingolipids and Sphingolipid Breakdown Products in Cellular Regulation", Science, 243, 500–506 (1989).
Herold, "Synthesis of D-erythro-and D-threo-Sphingosine Derivates from L-Serine", (71) pp. 354–362 (1988).
C. Hakomori, S., "Glycosphingolipids In Cellular Interaction, Differentiation, and Oncogenesis", Am. Rev. Biochem. 50, 733–739 (1981).
Kratzer et al., "An Efficient Synthesis of Sphingosine-1-Phosphate," Tetrahedron Letters (34) 11, pp. 1761–1764 (1993).
Merrill, A. H., "Cell Regulation by Sphingosine and More Complex Sphingolipids", J. Bioenerg. Biomembr., 23, 83–104 (1991).
Ruan et al., "Chemical Synthesis of D-Erythro-Sphingosine-1-Phosphate and Its Inhibitory Effects on Cell Motility," Bioorganic & Medicinal Chemistry Letter (2) 9, pp. 973–978 (1992).
Stoffel, W. et al., "Enzymatic Synthesis of 1-Phosphate Esters of 4t-Sphingenine (Sphingosine), Sphinganine (Dihydrosphingosine), 4-Hydroxysphinganine (Phytosphingosine) and 3-Dehydrosphinganine by Erythrocytes", Hoppe-Seyer's Z. Physiol. Chem., 349, 635–642 (1970).

(List continued on next page.)

*Primary Examiner*—Mary C. Lee
*Assistant Examiner*—Michael G. Ambrose
*Attorney, Agent, or Firm*—Leydig, Voit & Mayer, Ltd.

[57] ABSTRACT

The present invention provides a series of non-toxic compounds which function to inhibit the activity of S-1-P aldolase in respect to its cleavage of S-1-P. These inhibitors are described by the compounds of formula I

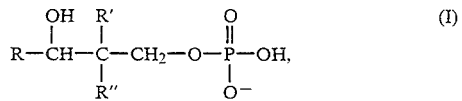

wherein R is a radical containing 1 to 15 carbon atoms, a halogen, or hydrocarbon, R' is an organic radical or hydrogen, and R" is —NH$_3$+ or —NH—NH +, with the proviso that, when R is CH$_3$(CH)$_{12}$(CH=CH) and R' is hydrogen, R" is —NH—NH$_3$+.

A method for preparing such compounds, which may generally be described as 1-phosphate derivatives of compounds which include a 2-amino-1,3-alcohol radical is also disclosed.

20 Claims, No Drawings

OTHER PUBLICATIONS

Stoffel, W. et al., "Chemistry and Biochemistry of 1-Desoxysphinganine 1-Phosphonate (Dihydrosphingosine-1-Phosphonate," Chem & Phys. of Lipids, 13, 372–388 (1974).

Van Veldhoven et al., "A Facile Enzymatic Synthesis of Sphingosine-1-Phosphate and Dihyrosphingosine-1-Phosphate," Journal of Lipid Research, (30), pp. 611–616 (1989).

Van Veldhoven, P. P. et al., "Subcellular Localization and Membrane Topology of Sphingosine-1-phosphate Lyase in Rat Liver", J. Biol. Chem., 266, 12502–12507 (1991).

Weiss, "Synthesis of Several Phosphorylated Derivates of Dihydrosphingosine," (79), pp. 5553–5557 (1957).

Westerdon et al., "An Approach to the Synthesis of a -L-Fucopyranosyl Phosphoric Mono-and Diesters Via Phosphite Intermediates", Tetrahedron Letters (27) 10, pp. 1211–1214 (1986).

Zhang, H. et al., "Sphingosine-1-Phosphate, a Novel Lipid, Involved in Cellular Proliferation", J. Cell Biol. 114, 155–167 (1991).

METHOD FOR PREPARATION OF SPHINGOID BASES

TECHNICAL FIELD OF THE INVENTION

The present invention relates to sphingoid bases, specifically, analogs of sphingosine-1-phosphate ("S-1-P"), and methods for their use, as well as to methods for the preparation of S-1-P and analogs thereof.

BACKGROUND OF THE INVENTION

Sphingolipids comprise a large class of biologically significant compounds, such compounds being constituents of cell membranes. The principal component of sphingolipids is almost invariably a particular long chain base, sphingosine.

When present in the cell, such sphingolipids are metabolized, yielding sphingosine as a metabolic intermediate. Interest in these metabolic intermediates in general, and sphingosine in particular, was heightened when it was realized that sphingosine was a potent and specific inhibitor of protein kinase C. Hakomori, S., Am. Rev. Biochem. 50, 733–739 (1981). This discovery was significant due to kinase C's known function as a pivotal regulatory enzyme in cell growth. E.g., Merrill, A. H., J. Bioenerg. Biomembr., 23, 83–104 (1991); Hannun, Y. A. et al., Science, 243, 500–506 (1989).

Recent research in the area of sphingosine and its analogs has demonstrated that one such analog has a significant effect on cell growth. More specifically, that analog, S-1-P, has proven to be a very potent mitogen in Swiss 3T3 fibroblasts. Zhang, H. et al., J. Cell Biol. 114,155–167 (1991). S-1-P has further been shown to cause rapid translocation of calcium from intracellular stores, i.e., from $IP_3$-sensitive and $IP_3$-insensitive intercellular pools in permeabilized smooth muscle cells. Ghosh, T. K., Science, 248, 1653–1656 (1990).

That S-1-P possessed the foregoing properties, i.e., as a mitogen and calcium translocator, was surprising because it was previously thought that the major role of S-1-P was its involvement in the catabolic pathway for sphingosine. Specifically, in that pathway, S-1-P is produced from sphingosine by the action of a specific kinase which is resident in the cell cytoplasm. After its production, S-1-P is cleaved into 2-hexadecenal and ethanolamine-1-phosphate by sphingosine-1-phosphate aldolase, which is resident in the endoplasmic reticulum of the cell. Stoffel, W. et al., Hoppe-Seyer's Z. Physiol. Chem., 349, 635–642 (1970); Van Valdhoven, P. P. et al., J. Biol. Chem., 266, 12502–12507 (1991).

In order to advance the study of S-1-P, and in particular its mitogenic properties and role as a "secondary" messenger in causing calcium translocation, it would be beneficial to be able to synthesize S-1-P on a commercial scale. Known synthesis routes have proven inadequate for this purpose, however, hampering this investigation. In particular, presently available routes are exceedingly time consuming and, further, are only able to provide S-1-P in relatively low yields and/or quantities.

One known method for the preparation of S-1-P is by means of an enzymatic synthesis. This method comprises hydrolyzing sphingosylphosphorylcholine with phospholipase D isolated from *Streptomyces chromofuscus*. However, this method gives a mixture of D-erythro and L-threo isomers of S-1-P, which are not separable. Moreover, the quantity of S-1-P provided by this method is relatively low, i.e., milligram quantities. Van Veldohoven, P. et al., J. Lipids Res. 30, 611 (1989). In contrast, a recently reported chemical synthesis provides for the preparation of only the D-erythro isomer of S-1-P. This synthesis begins by preparing its "starting" material (a D-erythro-olefinic alcohol) from L-serine. The starting material has both primary and secondary hydroxyl functionalities, as well as an amino functionality. Once the starting material is prepared, the synthesis proceeds by protecting both the amino and secondary hydroxyl functionalities of that material. The primary hydroxyl functionality, which is left unprotected, is then modified by phosphorylation, with the amino and secondary hydroxyl protective groups being subsequently removed to provide the aforesaid S-1-P isomer. While this synthesis provides only a single isomer of S-1-P, the synthesis remains lengthy (10 steps from L-serine to S-1-P, requiring about 98 hours to complete) and provides S-1-P in a relatively low yield (about 10.7%). Ruan, F., Bioorg. & Med. Chem. Let., 2 (9), 973–978 (1992).

A more recent chemical synthesis prepares S-1-P using a particular "starting" compound, namely 3-O-tertbutyldimethylsilyl ("TBDMS") protected D-erythroazidosphingosine ("the azido compound"). More specifically, the azido compound, which has primary and secondary hydroxyl functionalities as well as an azido functionality, is prepared from D-glucose in a nine step process at a yield of 15%, resulting in protection of the secondary hydroxyl functionality by the TBDMS group.

Once the azido compound has been prepared, its amino functionality is also protected using a carbonate compound. The primary hydroxyl functionality of the resulting compound, which remains unprotected, is then phosphorylated using bis(2-cyanoethoxy)(diisopropylamino)phosphine to provide a phosphite intermediate. After oxidation of the intermediate, the groups protecting the secondary hydroxyl and amino functionalities are removed, providing S-1-P. Kratzer, B. et al, Tetra. Let., 34. (11), 1761–1764 (1993).

While this method provides S-1-P, the synthesis is quite lengthy (14 steps from D-glucose to S-1-P, requiring about 318 hours to complete) and provides S-1-P in only a relatively low yield (about 8.4% overall). In addition, the method requires the use of some hazardous chemicals, e.g. dioxane, as well as the use of sodium azide, a compound which is highly explosive, especially in the presence of halogenated solvents.

Returning to the subject of the S-1-P aldolase (which functions to cleave S-1-P into two compounds), the study of its role at the cellular level would be enhanced by the availability of compounds which would inhibit the activity of the aldolase. Such would aid in the isolation and purification of S-1-P aldolase, thus allowing experimentation with that enzyme to be readily undertaken. To date, there is believed to be only a single inhibitor of S-1-P aldolase reported in the literature, that being a sphingosine derivative referred to as dihydrosphingosine-1-phosphonate ("DS-1-P").

The article that discloses DS-1-P attributes its S-1-P aldolase-inhibiting property to the substitution of a $—CH_2—PO_3$ group for the ester linkage ($—CH_2—O—PO_3$) found on the S-1-P compound. This substitution is said to reduce the distance between the head phosphate group and the remainder of the compound, particularly in regard to the 2C and 3C carbon atoms. The shortening of the compound is said to be significant because it is well known that the steric requirements of S-1-P aldolase are highly specific toward the 2S, 3R configuration of S-1-P. Thus, assuming the function of the phosphate functionality is to bind the compound to a positively-charged group at an enzyme's surface, thereby supporting the correct orientation of the two optically active centers (C2 and C3), the aforedescribed reduction in distance between the phosphate functionality and the active centers should lead to strongly altered binding by electrostatic forces. The end result of this is said to be a reduction in the velocity of the phosphonate and a competitive inhibition of the S-1-P aldolase reaction. Despite DS-1-P's activity as a S-1-P aldolase inhibitor, however, it is unfortunately highly toxic, rendering it useless for experimentation at the cellular level. Stoffel, W. et al., *Chem. & Phys. of Lipids*, 13,372–388 (1974).

Thus, there exists a need for a process for preparing S-1-P and analogs thereof which is more amenable to production of S-1-P and its analogs on a commercial scale, specifically, by providing those compounds at greater yields and quantities in a shorter period of time, while minimizing the use of hazardous chemicals. Further, a need exists for a compound or compounds which would inhibit the activity of S-1-P aldolase, thereby aiding its isolation and purification as well as contributing to a greater understanding of the functions of that aldolase at the cellular level.

The present invention fulfills the foregoing needs by providing a process for preparing S-1-P and analogs thereof which is more amenable to production of those compounds on a commercial scale. Specifically, the process provides S-1-P (as well as its analogs) at a greater yield and quantity, as well as at a lower preparation time, as compared to known processes, while minimizing the use of hazardous chemicals. The invention further provides a series of non-toxic compounds which function to inhibit the activity of S-1-P aldolase in respect to its cleavage of S-1-P.

These and other objects and advantages of the present invention, as well as additional inventive features, will be apparent from the description of the invention provided herein.

BRIEF SUMMARY OF THE INVENTION

The present invention provides a series of non-toxic compounds which function to inhibit the activity of S-1-P aldolase in respect to its cleavage of S-1-P. These inhibitors are described by formula I

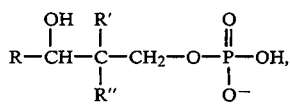

wherein R is a radical containing 1 to 15 carbon atoms, a halogen, or hydrogen, R' is an organic radical or hydrogen, and R" is —NH$_3^+$ or —NH—NH$_3^+$, with the proviso that, when R is CH$_3$(CH$_2$)$_{12}$(CH=CH)— and R' is hydrogen, R" is —NH—NH$_3^+$.

Another series of aldolase inhibitors provided by the present invention is described by the compound of formula II

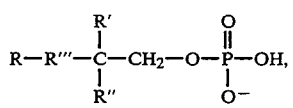

wherein R is a radical containing 1 to 15 carbon atoms, a halogen, or hydrogen, R' is an organic radical or hydrogen, R" is —NH$_3^+$ or —NH—NH$_3^+$, and R''' is a substituted or unsubstituted methylene radical, with the proviso that R''' is not —C(OH)H—.

The present invention further provides methods for inhibiting the cleavage of S-1-P by its aldolase in a reactive environment using either a compound of formula I, a compound of formula II, or mixtures thereof. The method comprises introducing a aldolase inhibiting amount of such a compound, or a mixture thereof, into a reactive environment which contains at least the aforesaid aldolase and S-1-P.

The present invention further provides a method for preparing a 1-phosphate derivative of a compound which includes a 2-amino-1,3-alcohol radical, i.e., a compound of formula I

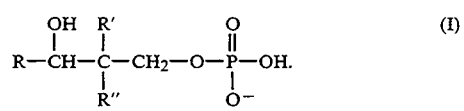

This method comprises (a) reacting each nitrogen of a compound of formula VII

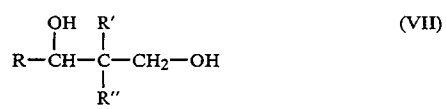

with a blocking compound to form an amine-blocked compound, wherein the 3-alcohol functionality is not blocked, (b) reacting the amine-blocked compound formed in step (a) with bis(2-cyanoethoxy)(diisopropylamino)phosphine, (c) oxidizing the compound formed in step (b) to form a phosphate triester, and (d) removing the cyanoethoxy groups and each blocking compound from the compound formed in step (c) to form the 1-phosphate derivative, wherein in respect to the compounds of formula I or formula VII, R is a radical containing 1 to 15 carbon atoms, a halogen, or hydrogen, R' is an organic radical or hydrogen, and R" is a radical comprising at least one nitrogen.

The present invention also provides a method for the preparation of S-1-P of formula III

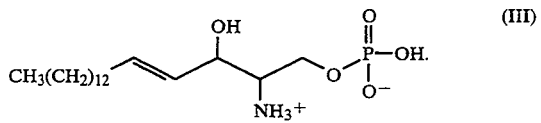

The method comprises (a) reacting the amine functionality of sphingosine of formula IV

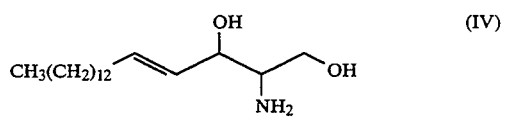

with a blocking compound Z to form an amino-blocked sphingosine of formula V

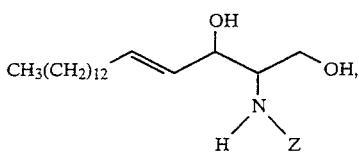

(V)

wherein the secondary hydroxyl functionality of the amino-blocked sphingosine is not blocked, (b) reacting the amino-blocked sphingosine of formula V with bis(2-cyanoethoxy) (diisopropylamino)phosphine and oxidizing the resulting compound to form a phosphate triester of formula VI,

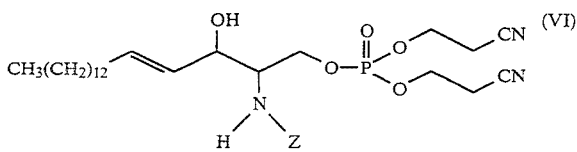

(VI)

and (c) removing the cyanoethoxy groups and the amine-blocking compound Z from the phosphate triester to form S-1-P.

DETAILED DESCRIPTION OF THE PREFERRED EMBODIMENTS

The present invention provides analogs of S-1-P and other related compounds which provide S-1-P aldolase-inhibiting properties, as well as methods for their preparation and use.

The compounds of the present invention which possess the aforesaid S-1-P aldolase-inhibiting properties are preferred because they are non-toxic when introduced into an environment which contains other cellular components, e.g., permeabilized cells. The only other known compound to possess such inhibitory properties in respect to S-1-P aldolase, DS-1-P, is a well known toxin in such environments.

The present inventive compounds, although related in structure, may be conveniently divided into two series to facilitate their description. The first series of compounds include those of formula I

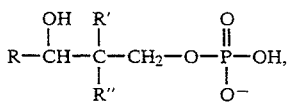

(I)

wherein R is a radical containing 1 to 15 carbon atoms, a halogen, or hydrogen, R' is an organic radical or hydrogen, and R" is $—NH_3^+$ or $—NH—NH_3^+$, with the proviso that, when R is $CH_3(CH_2)_{12}(CH=CH)—$ and R' is hydrogen, R" is $—NH—NH_3^+$. The proviso present in respect to the radical R", i.e., that when R is $CH_3(CH_2)_{12}(CH=CH)—$ and R' is hydrogen, R" is $—NH—NH_3^+$, is present to exclude the known compound S-1-P from being considered as a compound of the present invention.

As regarding formula I, R may be a substituted or unsubstituted alkane, alkene or alkyne radical and, more advantageously, a hydrocarbon radical. Preferably, R is a substituted or unsubstituted alkane hydrocarbon radical and, most preferably, R is the unsubstituted alkane hydrocarbon radical $CH_3(CH_2)_{14}—$.

The radical R' is advantageously an organic radical containing one or two carbon atoms and, most advantageously, a substituted or unsubstituted alkane, alkene or alkyne. Preferably, R' is a hydrocarbon radical and, most preferably, $—CH=CH_2$; $—CH_2F$; $—C\equiv CH$; or $—CH=CHF$.

In regard to formula I as a whole, when R is $CH_3(CH_2)_{14}—$ and R' and R" are defined as follows, a series of non-toxic aldolase-inhibiting analogs is provided: (a) R' is $—CH=CH_2$ and R" is $—NH_3^+$ (2-vinyl dihydrosphingosine-1-phosphate); (b) R' is H and R" is $—NH—NH_3^+$ (2-hydrazino deamino dihydrosphingosine-1-phosphate); (c) R' is $—CH_2F$ and R" is $—NH_3^+$ (2-fluoromethyl dihydrosphingosine-1-phosphate); (d) R' is $—C\equiv CH$ and R" is $—NH_3^+$ (2-ethynyl dihydrosphingosine-1-phosphate); and (e) R' is $—CH=CHF$ and R" is $—NH_3^+$ (2-fluorovinyl dihydrosphingosine-1-phosphate).

The second series of compounds provided by the present invention includes those of formula II

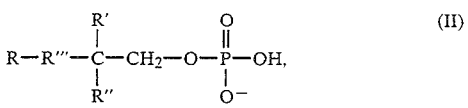

(II)

wherein R is a radical containing 1 to 15 carbon atoms, a halogen, or hydrogen, R' is an organic radical or hydrogen, R" is $—NH_3^+$ or $—NH—NH_3^+$, and R''' is a substituted or unsubstituted methylene radical, with the proviso that R''' is not $—C(OH)H—$. The proviso present in respect to the radical R", i.e., that R''' is not $—C(OH)H—$, is present to exclude those compounds of formula II that were previously included in the description of the compounds of formula I.

In regard to formula II, R, if it contains 1 to 15 carbon atoms, may advantageously be a substituted or unsubstituted alkane, alkene or alkyne radical, more advantageously a hydrocarbon radical. R is preferably, however, hydrogen or a halogen. Most preferably R is a halogen, with fluorine being the preferred halogen.

The component defined as R', which may be an organic radical as previously described in connection with the compounds of formula I, is advantageously hydrogen.

In regard to formula II as a whole, when R' is hydrogen and R, R", and R''' are defined as follows, a second series of non-toxic S-1-P aldolase-inhibiting analogs is provided: (a) R is fluorine, R" is $—NH_3^+$, and R''' is $—CHF—$ (2-difluoromethyl ethanolamine-O-phosphate); (b) R is fluorine, R" is $—NH_3^+$, and R''' is $—CH_2—$ (2-fluoromethyl ethanolamine-O-phosphate); and (c) R" is $—NH_3^+$ and R—R''' is $CH_2=CH—$ (2-vinyl ethanolamine-O-phosphate).

The present invention further includes methods for using the previously described compounds of the first (based upon the compound of formula I) and second (based upon the compound of formula II) series. More specifically, the invention provides a method for inhibiting the cleavage of sphingosine-1-phosphate by S-1-P aldolase in a reactive environment. The method comprises introducing an S-1-P aldolase inhibiting amount of a compound of formula I, a compound of formula II, or a mixture thereof, into the reactive environment which contains at least S-1-P aldolase and sphingosine-1phosphate. The various reactive environments under which the method can be successfully operated will be readily appreciated by those skilled in the art and include any suspension, emulsion, solution, permeabilized cells or the like in which S-1-P aldolase is capable of reacting with S-1-P to cleave said compound.

The present invention further provides a method which allows the preparation of S-1-P in a manner which is more amenable to the production of this compound on a commercial scale. Moreover, the method allows S-1-P to be prepared at a greater yield and greater quantity as well as in less time, as compared to known processes, while minimizing the use of hazardous chemicals.

The method for preparing sphingosine-1-phosphate of formula III

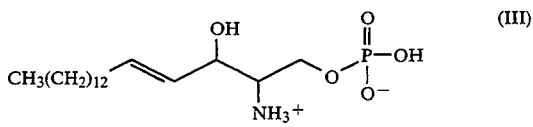

comprises (a) reacting the amine functionality of sphingosine of formula IV

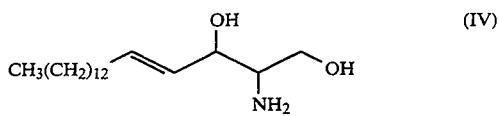

with a compound which comprises blocking group Z to form an amino-blocked sphingosine of formula V

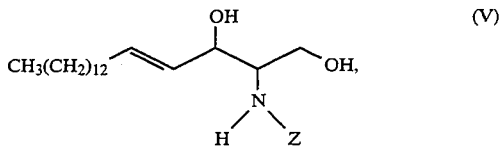

wherein the secondary hydroxyl functionality of the amino-blocked sphingosine is not blocked, (b) reacting the amino-blocked sphingosine of formula V with bis(2-cyanoethoxy) (diisopropylamino)phosphine and oxidizing the resulting compound to form a phosphate triester of formula VI,

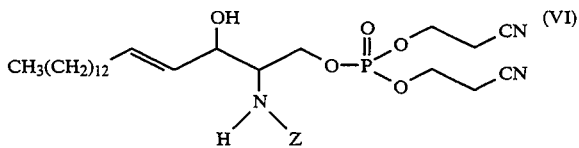

and (c) removing the cyanoethoxy groups and the amine-blocking group Z from the phosphate triester to form sphingosine-1-phosphate.

While the various reactants not specifically identified in the foregoing method may be selected from any of a number of compounds which provide the desired results, certain reactants are advantageously used in the foregoing method, in certain quantities. In particular, the amino-blocked sphingosine may be formed by reacting sphingosine with any number of suitable compounds which, upon bonding to the amine functionality of sphingosine, prevents that amine functionality from participating in the subsequent phosphorylation. Di-tert-butyl dicarbonate is preferred as the compound which comprises blocking group Z. In this preferred embodiment, the blocking group Z is t-butyl-carboxy. The dicarbonate is preferably provided in an amount which is in excess of the amount of sphingosine present, when measured on a molar basis. Most preferably, the molar ratio of the dicarbonate component to sphingosine is about 2:1. The phosphine component, which is reacted with the amino-blocked sphingosine, is preferably present in an amount which is approximately equivalent to the amount of amino-blocked sphingosine present, when measured on a molar basis. The cyanoethoxy groups are advantageously removed from the phosphate triester by reacting the phosphate triester with dimethylamine, which amine is provided in a quantity sufficient to completely remove both of the cyanoethoxy groups. Further, the blocking group on the amine functionality of the phosphate triester is advantageously removed by reacting the phosphate triester with trifluoroacetic acid. The acid should be provided in an amount sufficient to achieve the desired removal of the amine blocking group. The oxidation which provides the phosphate triester is advantageously completed using iodine.

The foregoing method is predicated at least in part upon the discovery that S-1-P can be prepared without requiring the 3-alcohol functionality of sphingosine to be protected (blocked) during at least the phosphorylation step. This recognition allowed S-1-P to be prepared directly from a commercially available compound, i.e., sphingosine.

The method of the present invention was surprising in that known processes taught that the phosphorylation step could be undertaken only when the secondary alcohol functionality of sphingosine, as well as its amino functionality, were blocked. Obtaining such a partially blocked sphingosine, however, was not simply a matter of appending the appropriate blocking compounds onto sphingosine. In fact, it is believed that no process for directly appending such blocking compounds onto sphingosine, or a process for the preparation of S-1-P which uses sphingosine as a starting compound, existed prior to the discovery of the present invention. The prior art instead uses a relatively complex multi-step synthesis that begins with compounds such as L-serine or D-glucose. Such synthesis, while providing the partially blocked sphingosine, provides S-1-P only at low yields while further requiring the use of hazardous chemicals.

In comparison, the present invention provides a method for the preparation of S-1-P which is not only readily adaptable to commercialization, but prepares S-1-P directly from a commercially available compound, sphingosine, at relatively substantial yields and quantities, in a lesser amount of time, and using relatively less harmful chemicals, as compared to known methods of preparing S-1-P.

The present invention also provides a more general method for preparing 1-phosphate derivatives of a compound which includes a 2-amino-1,3-alcohol radical. These derivatives, which are analogs of S-1-P, have been proven as, or based upon their analogous structure are expected to be, S-1-P aldolase inhibitors. This method provides the same benefits and advantages which are associated with the specific method for preparing S-1-P described previously.

The general method comprises (a) reacting each nitrogen of the compound of formula VII

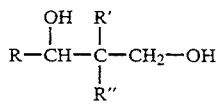

with a compound comprising an amine-blocking group to form an amine-blocked compound, wherein the 3-alcohol functionality is not blocked, (b) reacting the amine-blocked compound formed in step (a) with bis(2-cyanoethoxy)(diisopropylamino)phosphine, (c) oxidizing the compound formed in step (b) to form a phosphate triester, and (d) removing the cyanoethoxy groups and each amine-blocking group from the compound formed in step (c) to form the 1-phosphate derivative of formula I

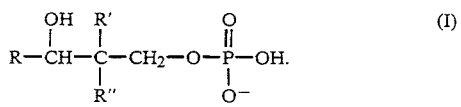

In the compounds of formulas I and VII, R is a radical containing 1 to 15 carbon atoms, a halogen, or hydrogen, R' is an organic radical or hydrogen, and R" is a radical comprising at least one nitrogen.

In the method, R in the compound of either formula I or VII is advantageously a substituted or unsubstituted alkane, alkene or alkyl radical, and is preferably a hydrocarbon radical. Most preferably, R in respect to the compound of formula VII is a substituted or unsubstituted alkane hydrocarbon radical.

The radical R' is advantageously an organic radical containing from one or two carbon atoms, most advantageously a substituted or unsubstituted alkane, alkene or alkyne radical, and preferably a hydrocarbon radical. Most preferably, that radical is —CH=CH$_2$; —CH$_2$F; —C≡CH; or —CH=CHF.

In regard to formula I and VII as a whole, when R in the compound of formula I is CH$_3$(CH$_2$)$_{14}$— and R' and R" in the compounds of either formula I or VII are defined as follows, a series of 1-phosphate derivatives of a compound which includes a 2-amino-1,3-alcohol radical is provided by the method of the present invention: (a) R' is —CH=CH$_2$ and R" is —NH$_3^+$ (2-vinyl dihydrosphingosine-1-phosphate); (b) R' is H and R" is —N-H—NH$_3^+$ (2 -hydrazino deamino dihydrosphingosine-1-phosphate); (c) R' is —CH$_2$F and R" is —NH$_3^+$ (2-fluoromethyl dihydrosphingosine-1-phosphate); (d) R' is —C≡CH and R" is —NH$_3^+$ (2-ethynyl dihydrosphingosine-1-phosphate); and (e) R' is —CH=CHF and R" is —NH$_3^+$ (2-fluorovinyl dihydrosphingosine-1-phosphate).

All of the compounds used in the foregoing methods are well known in the art. One reactant, bis(2-cyanoethoxy) (diisopropylamino)phosphine, which may not be commercially available, may be prepared by following the teachings provided in the art, e.g., Bannwarth, W., *Helv. Chim. Acta* 70, 175–186, 183 (1987).

The following examples further illustrate the present invention but, of course, should not be construed as in any way limiting its scope.

EXAMPLE 1

Preparation of Sphingosine-1-Phosphate(S-1-P).

Sphingosine (100 mg, 0.33 mmol), in solution in dry dichloromethane (15 mL), was combined with di-tert-butyl dicarbonate (144 mg, 0.66 mmol), the dicarbonate also being in solution in dry dichloromethane (10 mL). The solution containing the sphingosine and dicarbonate was then cooled to 0° C. under nitrogen. Diisopropylethylamine (85 mg, 0.66 mmol) was added to that solution in a dropwise manner. The solution was then stirred over an ice bath at 0° C. for 5 min., wherein at that point the ice bath was removed. The solution was stirred at room temperature for 5 h and subsequently diluted with dichloromethane (15 mL). The resulting organic layer was washed with water (2×10 mL), brine (20 mL), and dried over sodium sulfate. The solvent was then evaporated to provide a crude material, which was purified by flash chromatography eluted with a mixture of hexanes and ethyl acetate (3:2) to provide N-Boc sphingosine (partially blocked) (118 mg) at a yield of 90%.

Bis(2-cyanoethoxy) (diisopropylamino) phosphine (68 mg, 0.25 mmol), which was also in solution in dry acetonitrile (5 mL), was added to N-Boc sphingosine (100 mg, 0.25 mmol) in solution in dry dichloromethane (5 mL). Under argon, 1H-tetrazole (26 mg, 0.37 mmol) in solution in dry dichloromethane and acetonitrile (1:1 ratio, 4 mL) was slowly added to the phosphine/sphingosine solution. The resulting solution was stirred at room temperature for 50 min., wherein at that point iodine (0.4M in pyridine, water and dichloromethane in a 3:1:1 ratio) was added in a dropwise manner until the iodine was no longer decolorized (yellow color persisted). The solution was then stirred at room temperature for 15 min., and thereafter diluted with dichloromethane (25 mL), washed with a solution of sodium thiosulfate (5M, 2×10 mL), water (2×10 mL), and brine (15 mL). The organic layer of the solution was then dried over sodium sulfate, with the solvent being removed under vacuum, thereby providing a crude material. The crude material was purified by flash chromatography eluted with hexanes and ethyl acetate (1:1) to provide N-Boc sphingosine phosphate triester (111 mg) at a yield of 76%.

The aforesaid phosphate triester (100 mg, 0.17 mmol) in solution in dichloromethane (2 mL) was added to trifluoroacetic acid (2 mL). The resulting solution was stirred at room temperature for 1 h. The dichloromethane and trifluoroacetic acid were then removed under vacuum and the crude material dissolved in methanol (5 mL) and evaporated. This vacuum and evaporation sequence was then repeated. The crude material obtained thereby was treated with dimethylamine (30 mL, 40% in ethanol) and, after stirring at 45° C. for 6 h, the solvent was evaporated to dryness and the resulting crude dissolved in hot (boiled) acetic acid (1.5 mL). Water (1 mL) was added to the acetic acid solution, which was then cooled in an ice bath for 20 min. The material precipitated thereby was sedimented by centrifugation to provide a pellet. The pellet was then dispersed in water (3 mL) by sonication. The dispersed liquid was centrifuged at 4° C. for 10 min., with the water precipitation step being repeated. The solid material obtained was washed twice with acetone (2×3 mL) and twice with diethyl ether (2×5 mL). The final pellet formed thereby was dried under nitrogen, then under a vacuum for 12 h, to provide sphingosine-1-phosphate (38 mg) of formula III

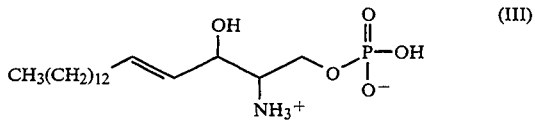

at a yield of 59%.

EXAMPLE 2

Preparation of Dihydrosphingosine-1-Phosphate (DS-1-P)

Dihydrosphingosine (100 mg, 0.33 mmol), in solution in dry dichloromethane (15 mL), was combined with di-tert-butyl dicarbonate (144 mg, 0.66 mmol), the dicarbonate also being in solution in dry dichloromethane (10 mL). The resulting solution was cooled to 0° C. by means of an ice bath under nitrogen, wherein thereafter diisopropylethylamine (85 mg., 20.66 mmol) was added in a dropwise manner. The solution was stirred at 0° C. for 5 min. wherein after which it was removed from the ice bath. The solution was subsequently stirred at room temperature for 5 h. The solution was then diluted with dichloromethane (15 mL), with the organic layer thereof being washed with water (2×10 mL) and brine (20 mL), and further being subsequently dried over sodium sulfate. The solvent was evaporated to provide a crude material which was purified by flash chromatography eluted with hexanes and ethyl acetate (3:2) to provide N-Boc dihydrosphingosine (104 mg) at a yield of 79%.

Bis(2-cyanoethoxy) (diisopropylamino) phosphine (68 mg, 0.25 mmol), in dry acetonitrile (5 mL), was added to N-Boc dihydrosphingosine (100 mg, 0.28 mmol), which was also in solution in dry dichloromethane (5 mL). Under an argon atmosphere, 1H-tetrazole (26 mg, 0.37 mmol) in solution in dry dichloromethane and acetonitrile (1:1, 4 mL) was slowly added to the phosphine and sphingosine solution. The resulting solution was stirred at room temperature for 50 min. Iodine (0.4M in pyridine, water and dichloromethane at a ratio of 3:1:1) was added to the solution in a dropwise manner until the iodine was no longer decolorized (yellow color persisted). The solution was stirred at room temperature for 15 min. and then diluted with dichloromethane (25 mL), washed with a solution of sodium thiosulfate (5M, 2×10 mL), water (2×10 mL), and brine (15 mL). The organic layer thereof was dried over sodium sulfate and the solvent removed under vacuum to provide a crude material which was purified by flash chromatography eluted with hexanes and ethyl acetate (1:1) to provide N-Boc dihydrosphingosine phosphate triester (104 mg) at a yield of 71%.

The dihydrosphingosine phosphate triester (90 mg, 0.15 mmol) in solution in dichloromethane (4 mL) was added to trifluoroacetic acid (4 mL). The resulting solution was then stirred at room temperature for 1 h. The dichloromethane and trifluoroacetic acid were subsequently removed under vacuum, with the resulting crude material being dissolved in methanol (5 mL) and then evaporated. The sequence involving subjecting the solution to a vacuum and evaporation was then repeated. The crude material obtained was treated with dimethylamine (30 mL, 40% in ethanol) and stirring at 45° C. for 6 h. The solvent was then evaporated to dryness and the crude dissolved in hot (boiled) acetic acid (1.5 mL). Water (1 mL) was added to the acetic acid solution, this being cooled in an ice bath for 20 min. The precipitated material prepared thereby was then sedimented by centrifugation to form a pellet. The pellet was dispersed in water (3 mL) by sonication, with the dispersion being centrifuged at 4° C. for 10 min. The aforedescribed water precipitation was then repeated. The solid material obtained thereby was washed twice with acetone (2×3 mL) and twice with diethyl ether (2×5 mL). The final pellet was dried under nitrogen, then under a vacuum for 12 h, to provide dihydrosphingosine-1-phosphate (30 mg) at a yield of 54%.

EXAMPLE 3

Preparation of 2-Hydrazino Deamino Dihydrosphingosine-1-Phosphate

A solution of palmitic chloride (15 g, 54.5 mmol) and $N_2O$-dimethylhydroxylamine hydrochloride (5.85 g, 60 mmol) was prepared in chloroform (130 mL). The solution was cooled to 0° C. and pyridine (9.5 g, 120 mmol) was added in a dropwise manner. After 2 h of stirring at room temperature, the solution was evaporated, the residue dissolved in diethyl ether (150 mL) and subsequently washed with cupric sulfate (10% aqueous solution, 2×40 mL) and brine (2×30 mL). The organic layer thereof was dried with sodium sulfate and concentrated. The crude material, was then purified by flash chromatography eluted with hexanes and ethyl acetate (80:20) to give pure N-methoxy-N-methyl-hexadecylamide (15.2 g) at a yield of 93%.

A solution of diisopropylamine (3 mL, 21.4 mmol) in tetrahydrofuran (20 mL) was cooled under nitrogen to −10° C., with n-butyllithium (2.5M in hexanes, 10 mL) being added thereto. After 20 min. of stirring at −10° C., the solution was cooled to −70° C. and ethyl acetate (1.78 mL, 18 mmol) in solution in tetrahydrofuran (3 mL) was added thereto. After 20 additional minutes at −70° C., a solution of N-methoxy-N-methyl-hexadecylamide (5.38 g, 18 mmol) in tetrahydrofuran (10 mL) was slowly added thereto. The solution was then stirred at −70° C. for 2 h and the temperature allowed to reach room temperature, at which point the solution was poured into hydrochloric acid (10%, 30 mL). The mixture was then extracted with diethyl ether (3×40 mL) and the combined organic layers were dried over sodium sulfate and evaporated to dryness. The residue was chromatographed through a column of silica gel, eluting with hexane and ethyl acetate (7:3) to provide ethyl-3-oxo octadecanoate (4.7 g) as an oil at a yield of 80%.

An ice-cold solution of ethyl-3-oxo octadecanoate (4 g, 12.27 mmol) in methanol (15 mL) was prepared. To this was added sodium borohydride (608 mg, 16 mmol). After the mixture was stirred for 40 min. at this temperature, the methanol was evaporated and the residue was portioned between hydrochloric acid (1N, 20 mL) and ethyl acetate (40 mL). The organic layer was washed with brine (15 mL), dried, and concentrated to provide 3.9 g of crude product. Further purification via flash chromatography on silica gel eluting with hexanes and ethyl acetate (3:2) provided ethyl-3-hydroxy octadecanoate (3.45 g) at a yield of 85%.

A solution of lithium diisopropylamide (12 mmol) in tetrahydrofuran (20 mL) was prepared. While stirring that solution at −60° C. under nitrogen, a solution of ethyl-3-hydroxy octadecanoate (1.64 g, 5 mmol) in tetrahydrofuran (10 mL) was added, the temperature thereof being allowed to reach −20° C. over a period of 40 min. The solution was then cooled to −70° C. and di-tert-butylazidocarboxylate (2.3 g, 10 mmol) in tetrahydrofuran (5 mL) was added thereto. This solution was quenched after 5 min. by the addition of acetic acid (5 mL). The solution was then stirred at −70° C. for 5 min., poured into water (10 mL), extracted with diethylether (2×20 mL), dried over sodium sulfate, and concentrated to yield a crude yellow oil which was purified by two successive columns (two flash chromatography columns were necessary in order to separate the product, ethyl-2-(N,N'-di-tert-butyloxy carbonyl)-hydrazino-3-hydroxy octadecanoate, from the by product, di-tert-butylhydrazidocarboxylate. The two flash chromatography columns were eluted with hexanes and ethyl acetate (3:1) to provide ethyl-2-(N,N'-di-tert-butyloxycarbonyl)-hydrazino-3-hydroxy octadecanoate (1.28 g) at a yield of 46%.

A solution of ethyl-2-(N,N'-di-tert-butyloxy carbonyl)-hydrazino-3-hydroxy octadecanoate (1.2 g, 2.15 mmol) in ethanol (15 mL) was prepared and cooled to −20° C. A suspension of calcium chloride (477 mg, 4.3 mmol) in tetrahydrofuran (20 mL), followed by sodium borohydride (327 mg, 8.6 mmol), was added thereto in small portions, with the temperature subsequently being allowed to reach room temperature. After 20 h, the solution was evaporated under reduced pressure and the residue dissolved in ethyl acetate (40 mL). The solution was then washed with hydrochloric acid (1N, 2×10 mL), saturated sodium chloride (25 mL), dried over sodium sulfate, and concentrated, yielding a crude material which was purified by flash chromatography eluted with hexanes and ethyl acetate (3:2) to provide 2-(N,N'-di-tert-butyloxy carbonyl)-hydrazino-1,3-actadecandiol (944 mg) at a yield of 90%.

Bis(2-cyanoethoxy)(diisopropylamino)phosphine (38 mg, 0.14 mmol) in dry acetonitrile (5 mL) was added to N₂O-Boc hydrazino deamino dihydrosphingosine (75 mg, 0.14 mmol), which was in solution in dry dichloromethane (5 mL). Under an argon atmosphere, 1H-tetrazole (15 mg, 0.21 mmol) in solution in dry dichloromethane and acetonitrile (at a ratio of 1:1, 4 mL) was slowly added to the phosphine/sphingosine solution. The solution was stirred at room temperature for 50 min. Iodine (0.4M in pyridine, water and dichloromethane at a ratio of 3:1:1) was added until the iodine was no longer decolorized (yellow color persisted). The solution was subsequently stirred at room temperature for 15 min., diluted with dichloromethane (20 mL), and washed with a solution of sodium thiosulfate (5M, 2×10 mL), water (2×10 mL) and brine (15 mL). The organic layer was then dried over sodium sulfate and the solvent removed under vacuum to provide a crude material which was purified by flash chromatography eluted with hexanes and ethyl acetate (1:1) to provide N,N'-Boc hydrazino deamino dihydrosphingosine phosphate triester (68 mg) at a yield of 69%.

N,N'-Boc hydrazino dihydrosphingosine phosphate triester (50 mg, 0.07 mmol) in solution in dichloromethane (2 mL) was added to trifluoroacetic acid (2 mL). The resulting solution was stirred at room temperature for 1 h. The dichloromethane and trifluoroacetic acid were then removed under vacuum, and the remaining crude material dissolved in methanol (5 mL) and evaporated. This vacuum and evaporation sequence was then repeated. The crude material obtained thereby was treated with dimethylamine (20 mL, 40% in ethanol) and, after stirring at 45° C. for 6 h, the solvent was evaporated to dryness and the crude dissolved in hot (boiled) acetic acid (1.5 mL). Water (0.8 mL) was then added to the acetic acid solution, which was subsequently cooled in an ice bath for 20 min. The material precipitated thereby was sedimented by centrifugation to form a pellet. That pellet was dispersed in water (3 mL) by sonication, with the dispersion being centrifuged at 4° C. for 10 min. The foregoing water precipitation sequence was twice repeated. The solid material obtained was washed twice with acetone (2×2 mL) and twice with diethyl ether (2×2 mL). The final pellet was dried under nitrogen, then under vacuum for 12 h, to provide 2-hydrazino deamino dihydrosphingosine-1-phosphate (15 mg) of formula VIII

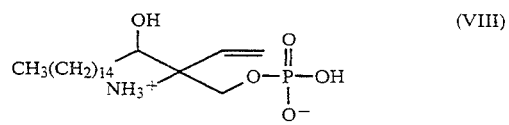

at a yield of 54%.

The in vitro biological evaluation of this compound indicated that it inhibited rat liver aldolase, with $IC_{50} = 0.8$ μM.

EXAMPLE 4

Preparation of 2-Vinyl Dihydrosphingosine-1-Phosphate

A solution of palmitic chloride (15 g, 54.5 mmol) and N₂O-dimethylhydroxylamine hydrochloride (5.85 g, 60 mmol) was prepared in chloroform (130 mL). The solution was cooled to 0° C. and pyridine (9.5 g, 120 mmol) was added in a dropwise manner. After 2 h stirring at room temperature, the solution was evaporated. The resulting residue was dissolved in diethylether (150 mL), washed with sodium sulfate (10% aqueous solution), and then with brine. The organic layer obtained thereby was dried over sodium sulfate and concentrated. Purification by flash chromatography eluted with hexanes and ethyl acetate (3:1) provided N-methoxy-N-methyl-hexadecylamide (15.2 g) at a yield of 93%.

A suspension of methionine methyl ester hydrochloride (3.8 g, 19 mmol) and freshly distilled benzaldehyde (2 g, 19 mmol) in dichloromethane (60 mL) was cooled to 0° C. and magnetically stirred. A solution of triethylamine (1.92 g, 19 mmol) in solution in dichloromethane (30 mL) was added slowly thereto. The resulting solution was allowed to stand overnight at room temperature, with stirring. After removal of the solvent, the residue was taken up in anhydrous diethyl ether, with the insoluble material being filtered off. The filtrate was washed with water (3×30 mL), brine (2×40 mL), dried over sodium sulfate, and concentrated, to provide a crude material which was purified by distillation (bp 144° C., 4 mm) providing methyl-2-(benzylideneamino)-4-(methylthio)butyrate (3.62 g) at a yield of 76%.

A solution of diisopropylamide (1.68 mL, 12 mmol) in tetrahydrofuran (12 mL) was treated at 0° C. with n-butyllithium (2.5M in hexanes, 4.8 mL, 12 mmol). After 20 min., the solution was cooled to −70° C., and treated with methyl-2-(benzylideneamino)-4-(methylthio)butyrate (2.5 g, 10 mmol) in tetrahydrofuran (8 mL). After 40 min. of stirring at −70° C., a solution of N-methoxy-N-methylhexadecylamide (2.9 g, 10 mmol) in tetrahydrofuran (25 mL) was added slowly thereto. The resulting solution was stirred for 2 h at −70° C., and then allowed to reach room temperature. The solution was then poured into water (20 mL) and extracted with diethyl ether (3×20 mL). The combined etheral layers were washed with brine, dried over sodium sulfate and evaporated to provide crude methyl 2-(benzylideneamino)-2-(3'-thiabutyl)-octadecanoate-3-one (4.6 g) at a yield of 94%. The yield calculation is based on the crude methyl 2-(benzylideneamino)-2-(3'-thiabutyl)-octadecanoate- 3-one material as the compound was not sufficiently stable for chromatography or distillation. Thus, methyl 2-(benzylideneamino)-2-(3'-thiabutyl)-octadecanoate-3-one was used for the next step without purification.

A mixture of crude methyl 2-(benzylideneamino)-2-(3'-thiabutyl)-octadecanoate-3-one (3 g, 6.13 mmol) in diethyl ether (20 mL) and hydrochloric acid (1N, 20 mL) was vigorously stirred at room temperature for 2 h. The diethyl ether phase was separated and evaporated to provide a hydrochloric amine salt. The crude amine hydrochloride was dissolved in hydrochloric acid (2N, 20 mL) and washed with n-hexane. The aqueous solution was concentrated under vacuum to provide a crude amino ester hydrochloride material. The crude amino ester hydrochloride in dichloromethane (40 mL) was then neutralized by use of a saturated solution of sodium bicarbonate (15 mL), with the resulting free base being purified by silica gel column chromatography eluted with hexane and ethyl acetate (9:1) to provide methyl 2-amino-2-(3'-thiabutyl)-octadecanoate-3one (1.82 g) at a yield of 74%.

A solution of methyl 2-amino-2-(3'-thiabutyl)-octadecanoate-3-one (2 g, 4.98 mmol) in dichloromethane (25 mL) was treated with trifluoroacetic anhydride (0.78 mL, 5.4 mmol). After 10 min., the solution was concentrated under reduced pressure and the residue was taken up in diethyl ether (50 mL), washed with water (2×20 mL), and dried over sodium sulfate to provide pure methyl 2-(3'-thiabutyl)-2-trifluroacteamido octadecanoate-3-one (2.4 g) at a yield of 96%.

A solution of methyl 2- (3'-thiabutyl) -2-trifluroacteamido octadecanoate-3-one (2 g, 4 mmol) in dichloromethane (20 mL) cooled to −40° C. was added to a solution of 85% m-chloroperbenzoic acid (811 mg, 4 mmol) in solution in dichloromethane (10 mL). The reaction between those two compounds was allowed to reach −10° C., wherein at that point the resulting solution was washed with saturated aqueous sodium bicarbonate (25 mL), dried over sodium sulfate, and evaporated. The resulting oil was purified by flash chromatography eluted with dichloromethane and diethyl ether (8:2) to form methyl 2-(ethylmethylsulfinyl)-2-trifluoroacetamido octadecanoate-3-one (1.95 g) at a yield of 95%.

A solution of methyl 2-(ethylmethylsulfinyl)-2-trifluoroacetamido octadecanoate-3-one (780 mg, 1.52 mmol) in xylenes (8 mL) was purged with nitrogen for 20 min. and heated in a sealed tube at 180° C. for 2 h. The solution was then allowed to cool to room temperature, placed in a dry ice bath for 10 min., and then at room temperature for 20 min. The solvent was subsequently evaporated under reduced pressure. The residue was purified by flash chromatography eluted with petroleum ether and ethyl acetate (8:2) to provide methyl 2-trifluoroacetamido-2-vinyloctadecanoate-3-one (460 mg) as a yellow oil at a yield of 66%.

A solution of methyl 2-trifluoroacetamido-2-vinyloctadecanoate-3-one (734 mg, 1.6 mmol) in ethanol (20 mL) cooled at −20° C., was added to a suspension of calcium chloride (890 mg, 8 mmol) in tetrahydrofuran (10 mL). Sodium borohydride (608 mg, 16 mmol) was then added in small portions and the temperature was allowed to reach room temperature. After 20 h, the solution was evaporated under reduced pressure and the residue dissolved in ethyl acetate (50 mL). The solution was then washed with hydrochloric acid (1N, 2×30 mL), saturated sodium chloride (20 mL), dried over sodium sulfate, and concentrated, yielding crude 2-vinyl dihydrosphingosine which was purified by flash chromatography eluted with chloroform and methanol (97:3), from which 2-vinyl dihydrosphingosine (430 mg) was obtained at a yield of 81%.

2-vinyl dihydrosphingosine (200 mg, 0.61 mmol) in solution in dry dichloromethane (15 mL) was added to di-tert-butyl dicarbonate (266 mg, 1.22 mmol) in solution in dry dichloromethane (12 mL). The resulting solution was cooled to 0° C. under nitrogen and diisopropyl ethylamine (157 mg, 1.22 mmol) was added thereto in a dropwise manner. The solution was then stirred at room temperature for 6 h and subsequently diluted with dichloromethane (30 mL). The organic phase thereof was washed with water (2×15 mL), and brine (20 mL) and dried over sodium sulfate. The solvent was then evaporated to provide a crude material which was purified by flash chromatography eluted with hexanes and ethyl acetate (3:2) to provide N-Boc 2-vinyl dihydrosphingosine (213 mg) at a yield of 82%.

Bis(2-cyanoethoxy)(diisopropylamino)phosphine (95 mg, 0.35 mmol) in dry acetonitrile (5 mL) was added to N-Boc 2-vinyl dihydrosphingosine (150 mg, 0.35 mmol) in solution in dry dichloromethane (5 mL). Under an argon atmosphere, 1H-tetrazole (36 mg, 0.52 mmol) in solution in dry dichloromethane and acetonitrile at a ratio of 1:1, 4 mL) was slowly added to the phosphine and sphingosine solution. The resulting solution was stirred at room temperature for 50 min. Iodine (0.4M in pyridine, water and dichloromethane at a ratio of 3:1:1) was added thereto until the iodine was no longer decolorized (yellow color persisted). The solution was then stirred at room temperature for 15 min. and diluted with dichloromethane (25 mL), washed with a solution of sodium thiosulfate (5M, 2×10 mL), water (2×10 mL), and brine (15 mL). The organic layer was dried over sodium sulfate and the solvent removed under vacuum, thereby providing a crude material which was purified by flash chromatography eluted with hexanes and ethyl acetate (1:1) to provide 2-vinyl dihydrosphingosine phosphate triester (165 mg) at a yield of 77%.

2-vinyl dihydrosphingosine phosphate triester (130 mg, 0.21 mmol) in solution in dichloromethane (5 mL) was added to trifluoroacetic acid (5 mL). The resulting solution was stirred at room temperature for 1 h. The dichloromethane and trifluoroacetic acid were then removed under vacuum and the crude material was dissolved in methanol (5 mL) and evaporated. This sequence was repeated. The crude material obtained thereby was treated with dimethylamine (35 mL, 40% in ethanol). After stirring at 45° C. for 6 h, the solvent was evaporated from the solution to dryness and the resulting crude dissolved in hot (boiled) acetic acid (2 mL). Water (1 mL) was added to the acetic acid solution, which was then cooled in an ice bath for 20 min. The precipitated material was sedimented by centrifugation to obtain in a pellet. The pellet was then dispersed in water (3 mL) by sonication and the dispersion centrifuged at 4° C. for 10 min. This water precipitation procedure was twice repeated. The solid material obtained thereby was washed with acetone (2×4 mL) and diethyl ether (2×5 mL). The final pellet was dried under nitrogen, and then under vacuum for 12 h, to provide 2-vinyl dihydrosphingosine-1-phosphate (52 mg) of formula IX

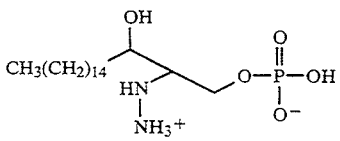

at a yield of 61%.

The in vitro biological evaluation of this compound indicated that it inhibited rat liver aldolase, with $IC_{50}=2.4$ $\mu$M. This compound was further determined to be a time dependent (irreversible) inhibitor of S-1-P aldolase.

EXAMPLE 5

Preparation of 2-Vinyl Ethanolamine-O-Phosphate

A suspension of 1.14 g (30 mmol) of lithium aluminum hydride in tetrahydrofuran (60 mL) was stirred at 0° C. as a solution of N-Boc methionine (2.63 g, 10 mmol) in tetrahydrofuran (20 mL) was added thereto. The resulting mixture was stirred at room temperature for 2 h and cooled to 0° C. Water (2 mL), sodium hydroxide (10%, 5mL), and water (3 mL) were added to the mixture in succession. The insoluble salts were then removed by filtration, and the filtrate was dried over sodium sulfate and concentrated. Purification of the resulting oil by chromatography on silica gel column chromatography eluted with diethyl ether and hexanes (1:1 to 3:1) as eluant provided 4-methyl sulfidinyl 2-N-tert-butyl carboxy-3-buten-1-ol (2.18 g) at a yield of 93%.

A solution of 4-methyl sulfidinyl 2-N-tert-butyl carboxy-3-buten-1-ol (2 g, 8.5 mmol) in dichloromethane (30 mL) cooled to −40° C. was added to a solution of 85% m-chloroperbenzoic acid (1.72 g, 8.5 mmol) in solution in dichloromethane (10 mL). The reaction between these compounds was allowed to reach −10° C., at which point the solution was washed with saturated aqueous sodium bicarbonate (2×15 mL), dried over sodium sulfate, and evaporated. The resulting sulfoxide was not purified, but subjected to thermal elimination as follows. The sulfoxide obtained in solution in xylenes (20 mL) was purged with nitrogen for 20 min. and heated in a sealed tube at 18° C. for 6 h. The solution was allowed to cool to room temperature, after which the solvent was evaporated under vacuum at 70° C. for 1 h. The residue was purified by flash chromatography eluted with hexanes and ethyl acetate (1:1) to provide 2-N-tert-butylcarboxy-3-buten-1-ol (1.03 g) at a yield of 65%.

Bis(2-cyanoethoxy)(diisopropylamino) phosphine (290 mg, 1.07 mmol) in dry acetonitrile (8 mL) was added to 2-N-tert-butylcarboxy-3-buten-1-ol (200 mg, 1.07 mmol) in solution in dry dichloromethane (7 mL). Under an argon atmosphere, 1H-tetrazole (112 mg, 1.6 mmol) in solution in dry dichloromethane and acetonitrile (1:1, 15 mL) was slowly added thereto. The resulting solution was stirred at room temperature for 40 min. Iodine (0.4M in pyridine, water and dichloromethane at a ratio of 3:1:1) was added in a dropwise manner until the iodine was no longer decolorized (yellow color persisted). The solution then was stirred at room temperature for 15 min. and diluted with dichloromethane (40 mL), wherein thereafter it was washed with a solution of sodium thiosulfate (5M, 2×15 mL), water (2×10 mL), and brine (20 mL). The organic layer was dried over sodium sulfate and the solvent removed under vacuum to provide a crude material which was purified by flash chromatography (30 g of silica gel, column dimensions 2×30 cm) eluted with hexanes and ethyl acetate (1:1) to provide N-Boc 2-vinyl ethanolamine phosphate triester (323 mg) at a yield of 80%.

N-Boc 2-vinyl ethanolamine phosphate triester (160 mg, 0.43 mmol) in solution in dichloromethane (3 mL) was added to trifluoroacetic acid (3 mL). The resulting solution was stirred at room temperature for 1 h. The dichloromethane and trifluoroacetic acid were then removed from the solution under vacuum and the crude material prepared thereby dissolved in methanol (5 mL) and evaporated. This sequence was repeated. The crude material obtained thereby was treated with dimethylamine (40 mL, 40% in ethanol). After stirring at 45° C. for 6 h, the solvent was evaporated to dryness and the crude was dissolved in ethanol (5 mL), evaporated, and this sequence repeated. The crude material obtained was purified by flash chromatography (30 g of silica gel, column dimensions, 2×25 cm) eluted with chloroform and methanol (98:2) providing 2-vinyl ethanolamine-O-phosphate (46 mg) of formula X

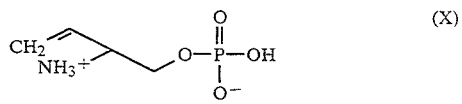

as a brown oil at a yield of 64%.

The in vitro biological evaluation of this compound indicated that it inhibited rat liver aldolase, with $IC_{50}=1.1$ $\mu$M. This compound was further determined to be a time dependent (irreversible) inhibitor of S-1-P aldolase.

EXAMPLE 6

Proposed Synthesis Route for 2-Fluoromethyl Dihydrosphingosine-1-Phosphate

A solution of palmitic chloride (15 g, 54.5 mmol) and N,O-dimethylhydroxylamine hydrochloride (5.85 g, 60 mmol) was prepared in chloroform (130 mL). The solution was cooled to 0° C. and pyridine (9.5 g, 120 mmol) was added in a dropwise manner. After 2 h stirring at room temperature, the solution was evaporated. The residue was dissolved in diethylether (150 mL), washed with sodium sulfate (10% aqueous solution) and then with brine. The organic layer was dried over sodium sulfate and concentrated. Purification by flash chromatography eluted with hexanes and ethyl acetate (3:1) yielded N-methoxy-N-methylhexadecylamide (15.2 g).

A suspension of methionine methyl ester hydrochloride (3.8 g, 19 mmol) and freshly distilled benzaldehyde (2 g, 19 mmol) in dichloromethane (60 mL) was cooled to 0° C. and magnetically stirred while triethylamine (1.92 g, 19 mmol) in solution in dichloromethane (30 mL) was added thereto. The reaction mixture was allowed to stand overnight at room temperature, with stirring. After removal of the solvent, the residue was taken up in anhydrous diethyl ether, and the insoluble material filtered off. The filtrate was washed with water (3×30 mL), brine (2×40 mL), dried over sodium sulfate, and concentrated to provide a crude material which was purified by distillation (bp 144° C., 4 mm) to yield methyl 2-(benzylideneamino)-4-(methylthio) butyrate (3.62 g).

A solution of diisopropylamine (1.68 mL, 12 mmol) in tetrahydrofuran (12 mL) was treated at 0° C. with n- butyllithium (2.5M in hexanes, 4.8 mL, 12 mmol). After 20 min., the solution was cooled to −70° C., and treated with methyl 2-(benzylideneamino)-4-(methylthio)butyrate (2.5 g, 10 mmol) in tetrahydrofuran (8 mL). After 40 min. of stirring at −70° C., a solution of amide N-methoxy-N-methylhexadecylamide (2.9 g, 10 mmol) in tetrahydrofuran (25 mL) was slowly added thereto. The solution was stirred for 2 h at −70° C., and then allowed to reach room temperature. The resulting liquid was poured into water (20 mL) and extracted with diethyl ether (3×20 mL). The combined etheral layers were washed with brine, dried over sodium sulfate and evaporated to provide a crude material (4.6 g) at a yield of 94%. (This yield is based on crude material; methyl2-(benzylideneamino)-2-(3'-thiabutyl)-octadecanoate3-one was not stable for chromatography or distillation. Thus, methyl 2-(benzylideneamino)-2-(3'-thiabutyl)-octadecanoate-3-one was used in the next step without purification).

A mixture of crude methyl 2-(benzylideneamino)-2-(3'-thiabutyl)-octadecanoate-3-one (3 g, 6.13 mmol) in diethyl ether (20 mL) and hydrochloric acid (1N, 20 mL) was vigorously stirred at room temperature for 2 h. The diethyl ether phase was separated and evaporated to provide the amine salt. The crude amine hydrochloride was dissolved in hydrochloric acid (2N, 20 mL) and washed with n-hexane. The aqueous solution was concentrated under vacuum to give crude amino ester hydrochloride. The crude material in dichloromethane (40 mL) was neutralized by saturated aqueous solution of sodium bicarbonate (15 mL), and the resulting free base purified by silica gel column chromatography eluted with hexane and ethyl acetate (9:1) to give methyl 2-amino-2-(3'-thiabutyl)-octadecanoate-3-one (1.82 g).

The remainder of this synthesis has not been experimentally verified. Accordingly, only a proposed route for the synthesis of 2-fluoromethyl dihydro sphingosine-1-phosphate from methyl 2-(3'-thiabutyl)-octadecanoate-3-one is provided.

Methyl 2-amino-2-(3'-thiabutyl)-octadecanoate-3-one is treated with 2 eq of di-tert-butyl dicarbonate followed with ethyldiisopropylamine (2 eq). The reaction solution is then stirred at room temperature for 6 h. The solution is diluted with dichloromethane and washed with water, brine, dried, evaporated to dryness, and purified by flash chromatography eluted with hexanes and ethyl acetate (1:1) to provide N-Boc ketoester.

The N-Boc ketoester is dissolved in methanol, and solid sodium borohydride (2 eq) is added thereto in small portions. The solution is stirred at room temperature for 2 h. The methanol is evaporated and the resulting crude dissolved in ethyl acetate. The solution is then washed with hydrochloric acid (2N), water, brine, and dried over sodium sulfate. The resulting crude material is purified by flash chromatography eluted with chloroform and methanol (95:5) to provide a β-hydroxy ester.

The β-hydroxy ester is dissolved in toluene and treated with dimethoxypropane (10 eq). P-toluensulfonic acid (0.1 eq) is added to the solution. The solution is refluxed at 120° C. for 4 h. The toluene is evaporated and the residue dissolved in diethylether, washed with a saturated solution of sodium bicarbonate, water, and brine. After drying and evaporation, the crude obtained is purified with flask chromatography eluted with hexanes and ethyl acetate (1:1) to provide an oxazolidine ester.

The oxazolidine ester is dissolved in dichloromethane and cooled to −40° C., wherein 1 eq. of m-chloroperbenzoic acid in solution in dichloromethane is added thereto. The temperature of the solution is then allowed to reach 0° C. The solution is diluted with dichloromethane, washed with sodium bicarbonate and water, dried and evaporated. The material obtained thereby is dissolved in xylenes and heated in a sealed tube at 180° C. The solution is allowed to reach room temperature, evaporated and chromatographed with flash chromatography eluted with hexanes and ethyl acetate (3:2) to provide 2-vinyl oxazolidine.

The 2-vinyl oxazolidine is dissolved in dichloromethane, purged with nitrogen for 10 min., and cooled to −70° C. A stream of ozone is passed through the solution when the TLC shows no starting material. A solution of sodium iodide (2 eq.) in acetic acid is added to reduce the peroxide product of ozonolysis and methanolysis and, after 1 h of stirring, the released iodine is reduced with sodium thiosulfate. The solution is washed with water, brine and evaporated to provide a compound.

To an ice-cold solution of that compound in tetrahydrofuran is added lithium aluminum hydride (1 eq in tetrahydrofuran). The solution is stirred at 0° C. for 1 h and poured into 10 mL of hydrochloric acid (0.5%). The aqueous phase is extracted with diethylether and the combined etheral phases are washed with water and brine. The crude material is purified by flash chromatography eluted with chloroform and methanol (97:3) to provide β-hydroxy ester.

Diethylaminosulfur trifluoride (DAST) (1.3 eq.) is carefully added to a solution of oxazolidine β-hydroxy ester in chloroform while under nitrogen. The solution is stirred at room temperature and poured into cold water. The organic layer is separated and the aqueous layer is extracted with chloroform. The combined chloroform is washed with brine, dried over sodium sulfate, and evaporated to dryness. Purification on flask chromatography yields 2-fluoromethyl oxazolidine ester.

A solution of 2-fluoromethyl oxazolidine ester is dissolved in methanol and p-toluensulfonic acid (0.2 eq.) added thereto. The solution is stirred at 75° C. The solution is then allowed to reach room temperature and the solvent evaporated. The residue is dissolved in dichloromethane, and washed with sodium bicarbonate, water and brine. The solvent is subsequently evaporated and the crude is purified by flash chromatography to provide N-Boc 2-fluoromethyl β-hydroxy.

N-Boc 2-fluoromethyl β-hydroxy in a solution in tetrahydrofuran is added to a solution of lithium aluminum hydride in tetrahydrofuran which had been cooled to 0° C. The mixture is stirred at 0° C. until no starting material is detected by thin layer chromatography. The solution is poured into hydrochloric acid (2N) and extracted with diethylether. The etheral layers are washed with water and brine, dried and evaporated to yield crude N-Boc 2-fluoromethyl, which is purified by flash chromatography.

N-Boc 2-fluoromethyl are dihydrosphingosine (1 eq.) in solution in dry dichloromethane is added to bis(2-cyanoethoxy((diisopropylamino)phosphine in dry acetonitrile. Under argon, 1H-tetrazole (1.5 eq) in solution in dry dichloromethane and acetonitrile (1:1) is slowly added thereto. The solution is stirred at room temperature for 50 min. Iodine (0.4M in pyridine, water and dichloromethane (3:1:1)) is added until it is no longer decolorized (yellow color persisted). The solution is then stirred at room temperature for 15 min. and diluted with dichloromethane, washed with a solution of sodium thiosulfate (5M), water and brine. The organic layer is dried over sodium sulfate and the solvent removed under vacuum to provide a crude material which is purified by flash chromatography eluted with hexanes and ethyl acetate (1:1) to provide N-Boc 2-fluoromethyl dihydrosphingosine phosphate triester.

Trifluoroacetic acid is added to N-Boc 2-fluoromethyl dihydrosphingosine phosphate triester in solution in dichloromethane. The solution is stirred at room temperature for 1 h. The dichloromethane and trifluoroacetic acid are removed under vacuum and the crude material dissolved in methanol and evaporated. This sequence is then repeated. The crude material obtained is treated with dimethylamine (40% in ethanol). After stirring at 45° C. for 6 h, the solvent is evaporated to dryness and the crude dissolved in hot (boiled) acetic acid. Water is added to the acetic acid solution which is then cooled in an ice bath for 20 min. The precipitated material is sedimented by centrifugation. The pellet obtained thereby is dispersed in water by sonication wherein thereinafter the solution is centrifuged at 4° C. for 10 min. This water precipitation process is twice repeated. The solid material obtained thereby is washed twice with acetone and twice with diethyl ether. The final pellet obtained is dried under nitrogen and then under vacuum for 12 h to provide 2-fluoromethyl dihydrosphingosine-1-phosphate of formula XI

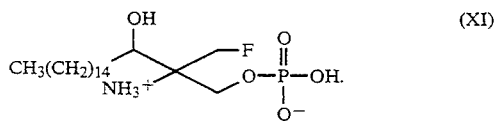

EXAMPLE 7

Proposed Synthesis Route for 2-Ethynyl Dihydrosphingosine-1-Phosphate

This synthesis has not been experimentally verified. Accordingly, this example consists only of a proposed route for the preparation of 2-ethynyl dihydrosphingosine-1-phosphate.

One eq. of benzaldehyde is added to 3-trimethylsilylpropargylamine in dichloromethane, followed by the dropwise addition of triethylamine (1.1 eq) thereto. The solution is stirred at room temperature for 12 h. Subsequently, the solution is washed twice with water and twice with brine, dried over sodium sulfate, and the solvent evaporated to yield 3-trimethylsilyl propargyl benzylidenamine.

n-butyllithium in solution in hexanes is added in a dropwise manner to a solution of 3-trimethylsilyl benzylidenamine in solution in THF. After 30 min. of stirring at −70° C., palmitoyl chloride (1 eq.) in solution in THF is added thereto. The solution is stirred at −70° C. for 30 min., and lithium diisopropylamine (1 eq.) in solution in hexanes is added in a dropwise manner. After 20 min. of stirring at −70° C., a solution of methyl chloroformate in tetrahydrofuran is added thereto. The solution is stirred at −70° C. for 20 min. and poured into diethylether. The solution is then washed with water and brine, dried over sodium sulfate, and concentrated to yield palmitoyl propargylamine benzylidenamine.

Crude palmitoyl propargylamine benzylidenamine is dissolved in diethyl and hydrochloric acid (5N) is added. After 2 h of stirring at room temperature, the etheral phase is separated and evaporated. The crude obtained is dissolved in hydrochloric acid (2N) and washed with hexane. The aqueous phase is evaporated and dissolved in dichloromethane which is washed with sodium bicarbonate, dried over sodium sulfate, and evaporated to yield the 2-trimethylsilylpropargyl α-amino β-ketoester, which is purified by flash chromatography.

Di-tert-butyl dicarbonate (2 eq.) followed by 2 eq. of ethyldiisopropylamine are added to the 2-trimethylsilylpropargyl α-amino β-ketoester in solution in dichloromethane. The solution is stirred at room temperature for 5 h and diluted with dichloromethane, washed twice with water, dried, and evaporated. The resulting protected amine, N-Boc 2-trimethylsilylacetylene D-keto ester, is purified by flash chromatography.

1.2 eq. of sodium methoxide is added to N-Boc 2-trimethylsilylacetyleno β-keto in methanol. The resulting solution is stirred at 20° C. for 30 min. The solution is subsequently evaporated and dissolved in diethylether, washed several times with water, dried over sodium sulfate, and evaporated. The resulting crude material is purified by flash chromatography eluted with 10% of acetone in chloroform.

Calcium chloride (2 eq.) in solution in tetrahydrofuran is added to the aforesaid crude material dissolved in tetrahydrofuran and ethanol (1:1). After cooling the solution to −20° C., solid sodium borohydride (4 eq) is added in small portions. The solution is stirred overnight, allowing the reaction temperature to reach room temperature. The solvents are evaporated under vacuum and the residue dissolved in ethylacetate and washed with hydrochloric acid (2N), water and brine. The crude material is purified by flash chromatography to yield pure N-Boc 2-ethynyl dihydrosphingosine.

N-Boc 2-ethynyl dihydrosphingosine-1-phosphate (1 eq.) in solution in dry dichloromethane is added to bis(2-cyanoethoxy)(diisopropylamino) phosphine in dry acetonitrile. Under argon, 1H-tetrazole (1.5 eq) in solution in dry dichloromethane and acetonitrile (1:1) is slowly added thereto. The solution is stirred at room temperature for 50 min. Iodine (0.4M in pyridine, water and dichloromethane (3:1:1)) is added to the solution until the iodine is no longer decolorized (yellow color persisted). The solution is stirred at room temperature for 15 min. and diluted with dichloromethane, washed with a solution of sodium thiosulfate (5M), water, and brine. The organic layer is dried over sodium sulfate and the solvent removed under vacuum to provide a crude material which is purified by flash chromatography eluted with hexanes and ethyl acetate (1:1), providing N-Boc 2-ethynyl dihydrosphingosine-1-phosphate triester.

Trifluoroacetic acid is added to the N-Boc 2-ethynyl dihydrosphingosine-1-phosphate triester in solution in dichloromethane. The solution is stirred at room temperature for 1 h. The dichloromethane and trifluoroacetic acid are removed under vacuum and the crude material is dissolved in methanol and evaporated. This sequence is then repeated. The crude material obtained is treated with dimethylamine (40% in ethanol) and, after stirring at 45° C. for 6 h, the solvent evaporated to dryness. The crude is then dissolved in hot (boiled) acetic acid. Water is added to the acetic acid solution which is cooled in an ice bath for 20 min. to form a precipitate. The precipitated material is sedimented by centrifugation. The pellet obtained thereby is then dispersed in water by sonication. The resulting solution was centrifuged at 4° C. for 10 min. This water precipitation is repeated twice. The solid material thus obtained is washed twice with acetone and twice with diethyl ether. The final pellet is dried under nitrogen, then under vacuum for 12 h to provide 2-ethynyl dihydrosphingosine-1-phosphate of formula XII

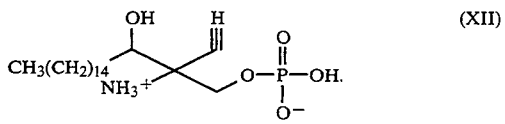

EXAMPLE 8

Proposed Synthesis Route for 2-Fluorovinyl Dihydrosphingosine-1-Phosphate

Methyl 2-amino-2-(3'-thiabutyl)-octadecanoate-3-one was prepared according to the procedure set forth in Example 6. Thereafter, a solution of methyl 2-amino-2-(3'-thiabutyl)-octadecanoate-3-one (2 g, 4.98 mmol) in dichloromethane (25 mL) was treated with trifluoroacetic anhydride (0.78 mL, 5.4 mmol). After 10 min., the solution was concentrated under reduced pressure and the residue was taken up in diethyl ether (50 mL), washed with water (2×20 mL) and dried over sodium sulfate. This yielded pure methyl 2-(3'-thiabutyl)-2-trifluoroacetamido octadecanoate-3-one.

The remainder of this synthesis has not been experimentally verified. Accordingly, only a proposed route for the synthesis of 2-fluorovinyl dihydrosphingosine-1-phosphate from methyl 2-(3'-thiabutyl)-2-trifluoroacetamido octadecanoate-3-one is provided.

Methyl 2-(3'-thiabutyl)-2-trifluoroacetamido octadecanoate-3-one dissolved in acetonitrile is treated with 1 eq. of SELECTFLUOR (F-TEDA-BF$_4$) at room temperature for 2 h, the solution diluted with dichloromethane, washed with water, brine, dried and evaporated to yield crude (fluoromethylsulfinyl) β-ketoester which is purified by flash chromatography.

M-chloroperbenzoic acid (1 eq.) in solution in dichloromethane is added to (fluoromethylsulfinyl) β-ketoester dissolved in dichloromethane cooled to −40° C. The temperature of the mixture is allowed to reach 0° C. The solution is then diluted with dichloromethane and washed with sodium bicarbonate, water, dried and evaporated. The material obtained is dissolved in xylenes and heated in a sealed tube at 180° C. for 2 h. The solution is allowed to reach room temperature, evaporated and chromatographed with flash chromatography eluted with hexanes and ethyl acetate (3:2) to provide 2-fluorovinyl keto ester.

Calcium chloride (2 eq.) in solution in tetrahydrofuran is added to the 2-fluorovinyl keto ester which is dissolved in tetrahydrofuran and ethanol (1:1). After cooling the solution to −20° C., solid sodium borohydride (4 eq.) is added in small portions. The solution is then stirred overnight while allowing the reaction mixture to reach room temperature. The solvents are subsequently evaporated under vacuum and the residue is dissolved in ethylacetate and washed with hydrochloric acid (2N), water and brine. The solution is dried and evaporated, yielding crude 2-fluorovinyl dihydrosphingosine which is purified by flash chromatography.

Di-tert-butyl dicarbonate (2 eq.) is added to 2-fluorovinyl dihydrosphingosine in dichloromethane followed by diisopropylethylamine (2 eq.). The solution is stirred at room temperature and diluted with dichloromethane. The solution is washed with water, brine, dried and evaporated to provide crude N-Boc 2-fluorovinyl dihydrosphingosine, which is then purified by flash chromatography.

N-Boc 2-fluorovinyl dihydrosphingosine (1 eq.) in solution in dry dichloromethane is added to bis(2-cyanoethoxy)(diisopropylamino) phosphine in dry acetonitrile. Under argon, 1H-tetrazole (1.5 eq) in solution in dry dichloromethane and acetonitrile (1:1) is slowly added thereto. The solution is stirred at room temperature for 50 min. Iodine (0.4M in pyridine, water and dichloromethane (3:1:1)) is added dropwise until the iodine is no longer decolorized (yellow color persisted). The solution is then stirred at room temperature for 15 min. and diluted with dichloromethane, washed with a solution of sodium thiosulfate (5M), water and brine. The organic layer is dried over sodium sulfate and the solvent removed under vacuum to provide a crude material which is purified by flash chromatography eluted with hexanes and ethyl acetate (1:1) to provide N-Boc 2-fluorovinyl dihydrosphingosine-1-phosphate triester.

Trifluoroacetic acid is added to 2-fluorovinyl dihydrosphingosine-1-phosphate in solution in dichloromethane. The solution is stirred at room temperature for 1 h. The dichloromethane and trifluoroacetic acid are then removed under vacuum and the crude material is dissolved in methanol and evaporated. This sequence is repeated. The crude material obtained thereby is treated with dimethylamine (40% in ethanol) and after stirring at 45° C. for 6 h, the solvent is evaporated to dryness and the crude dissolved in hot (boiled) acetic acid. Water is added to the acetic acid solution, which is then cooled in an ice bath for 20 min. The precipitated material is then sedimented by centrifugation. The pellet obtained is dispersed in water by sonication, with the solution being centrifuged at 4° C. for 10 min. This water precipitation procedure is twice repeated. The solid material obtained is washed twice with acetone and twice with diethyl ether. The final pellet is dried under nitrogen, and then under vacuum for 12 h, to provide 2-fluorovinyl dihydrosphingosine-1-phosphate of formula XIII

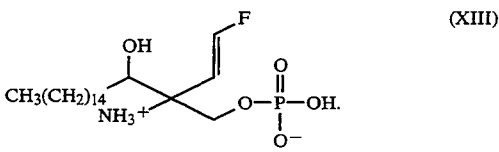

EXAMPLE 9

Proposed Synthesis Route for 2-Difluoromethyl Ethanolamine-O-Phosphate

This synthesis has been only partially experimentally verified. Accordingly, this example consists of a proposed route for the preparation of 2-difluoromethyl ethanolamine-O-phosphate.

A solution of (Boc)$_2$O (2 g, 9.17 mmol) in dichloromethane was added to an ice-cold solution of serine i0 methyl ester (0.93 g, 6 mmol) in dichloromethane (40 mL) in the presence of diisopropylethylamine (1.18 g, 9.17 mmol). After 4 h stirring at room temperature, the solution was diluted with dichloromethane, washed with water and brine. After drying and evaporation, a pure N-Boc serine methyl ester (1.3 g) is obtained.

A solution of N-Boc serine methyl ester (1.2 g, 5.48 mmol), dimethoxypropane (2.85 g, 27.4 mmol), and p-TSOH-H$_2$O (95 mg, 0.5 mmol) in toluene (50 ml) was heated under reflux (120° C.) for 2 h. Toluene was distilled off and replaced with 100 mL of diethylether. The solution was dried and concentrated to give the crude product as a brown oil which was purified with flash chromatography eluted with hexanes and ethyl acetate (4:1) to provide oxazolidine (1.29 g).

A −78° C. solution of DIBAL-H in toluene (1.5M, 2 mL) is added to a stirred −78° C. solution of oxazolidine 31 (1.1 g, 4.2 mmol) in dry toluene (30 mL). The mixture was stirred at −78° C. for 2 h and quenched by slowly adding 2 mL of cold (−78° C) methanol. The resulting residue was poured into 30 mL of hydrochloric acid (1N) and the mixture extracted with ethyl acetate (3×30 mL). The combined organic layers were washed with brine (2×40 mL), dried with sodium sulfate, and concentrated in vacuum. The crude material was purified by flash chromatography eluted with hexanes and ethyl acetate to provide an aldehyde (0.8 g).

The remainder of the synthesis consists of a proposed route for the preparation of 2-difluromethyl ethanolamine-o-phosphate from the aldehyde.

Diethylaminosulfur trifluoride (DAST) is added to a stirred solution of the aldehyde in ethanol free chloroform. The solution is stirred at room temperature and poured into an ice-cold hydrochloric acid (1N) solution. The aqueous phase is extracted with chloroform and the combined organic phases are washed with water, dried, and concentrated. The derivative is purified by flash chromatography, yielding pure difluoro methyl oxazolidine.

A solution of difluoro methyl oxazolidine is dissolved in methanol with p-toluensulfonic acid (0.2 eq) being added thereto. The solution is stirred at 75° C. Thereafter, the solution is allowed to reach room temperature and the solvent evaporated. The residue is dissolved in dichloromethane, washed with sodium bicarbonate, water and brine. The solvent is then evaporated and the crude is purified by flash chromatography to provide N-Boc difluoromethyl ethanolamine.

N-Boc difluoromethyl ethanolamine (1 eq) in solution in dry dichloromethane is added to bis(2-cyanoethoxy)(diisopropylamino)phosphine in dry acetonitrile. Under argon, 1H-tetrazole (1.5 eq) in solution in dry dichloromethane and acetonitrile (1:1) is slowly added thereto. The solution is stirred at room temperature for 50 min. Iodine (0.4M in pyridine, water and dichloromethane (3:1:1)) is added until the iodine is no longer decolorized (yellow color persists). The solution is then stirred at room temperature for 15 min. and diluted with dichloromethane, washed with a solution thiosulfate (5M), water and brine. The organic layer is dried over sodium sulfate, with the solvent being removed under vacuum to provide a crude material which is purified by flash chromatography eluted with hexanes and ethyl acetate (1:1) to provide N-Boc 2-difluoromethyl ethanolamine-O-phosphate triester.

Trifluoroacetic acid is added to N-Boc 2-difluoromethyl ethanolamine-O-phosphate triester in solution in dichloromethane. The solution is stirred at room temperature for 1 h. The dichloromethane and trifluoroacetic acid are removed under vacuum and the crude material dissolved in methanol and evaporated. This sequence is then repeated. The crude material obtained is treated with dimethylamine (40% in ethanol) and, after stirring at 45° C. for 6 h, the solvent is evaporated to dryness and the crude dissolved in ethanol and evaporated. This sequence is then repeated. The crude obtained is purified by flash chromatography eluted with chloroform and methanol (95:5) to yield pure 2-difluoromethyl ethanolamine-O-phosphate of formula XIV

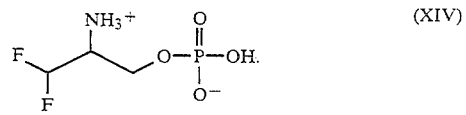

EXAMPLE 10

Proposed Synthesis Route for 2-Fluoromethyl Ethanolamine-O-Phosphate

This synthesis has been only partially experimentally verified. Accordingly, this example consists of a proposed route for the preparation of 2-fluoromethyl ethanolamine-O-phosphate.

The oxazolidine is prepared according to procedure set forth in Example 9. The remainder of this synthesis consists of a proposed route for the preparation of 2-fluoromethyl ethanolamine-O-phosphate from oxazolidine.

Thereafter, a solution of 2M lithium aluminum hydride in tetrahydrofuran (3 mL) was added to a stirred −78° C. solution of oxazolidine (800 mg, 3.08 mmol) in dry tetrahydrofuran (40 mL). The reaction mixture was stirred at 0° C. for 20 min. and allowed to reach room temperature. After stirring for 2 h, the solution was poured into an ice-cold hydrochloric acid (2N, 20 mL). The resulting residue was extracted with ethyl acetate (3×40 mL). The combined organic layers were then washed with brine (2×20 mL), dried with sodium sulfate, and concentrated in vacuum. The crude material was purified by flash chromatography eluted with hexanes and ethyl acetate (1:1) to provide an alcohol (503 mg).

Diethylaminosulfur trifluoride (DAST) is added to a stirred solution of the alcohol in ethanol free chloroform. The solution is stirred at room temperature and poured into ice-cold hydrochloric acid (1N). The aqueous phase is extracted with chloroform and the combined organic phases are washed with water, dried and concentrated. The difluoro derivative, fluoromethyl oxazolidine, is purified by flash chromatography.

A solution of fluoro methyl oxazolidine is dissolved in methanol to which p-toluensulfonic acid (0.2 eq) is added. The solution is stirred at 75° C. The solution is then allowed to reach room temperature and the solvent evaporated. The residue is dissolved in dichloromethane, washed with sodium bicarbonate, water and brine. The solvent is evaporated and the crude N-Boc fluoromethyl ethanolamine is purified by flash chromatography.

N-Boc fluoromethyl ethanolamine (1 eq) in solution in dry dichloromethane is added to bis(2-cyanoethoxy)(diisopropylamino) phosphine in dry acetonitrile. Under argon, 1H-tetrazole (1.5 eq) in solution in dry dichloromethane and acetonitrile (1:1) is slowly added. The solution is then stirred at room temperature for 50 min. Iodine (0.4M in pyridine, water and dichloromethane (3:1:1)) is added until the iodine is no longer decolorized (yellow color persisted). The solution is then stirred at room temperature for 15 min., diluted with dichloromethane, and washed with a solution of sodium thiosulfate (5M), water and brine. The organic layer is dried over sodium sulfate and the solvent removed under vacuum to provide a crude material which is purified by flash chromatography eluted with hexanes and ethyl acetate (1:1) to provide pure N-Boc 2-fluoromethyl ethanolamine-O-phosphate triester.

Trifluoroacetic acid is added to N-Boc 2-fluoromethyl ethanolamine-O-phosphate triester in solution in dichloromethane. The solution is stirred at room temperature for 1 h. The dichloromethane and trifluoroacetic acid are then removed under vacuum and the crude material is dissolved in methanol and evaporated. This sequence is then repeated. The crude material obtained thereby is treated with dimethylamine (40% in ethanol) and, after stirring at 45° C. for 6 h, the solvent is evaporated to dryness and the crude dissolved in ethanol and evaporated. This sequence is repeated. The crude obtained thereby is purified by flash chromatography eluted with chloroform and methanol (95:5) to yield pure 2-fluoromethyl ethanolamine-O-phosphate of formula XV

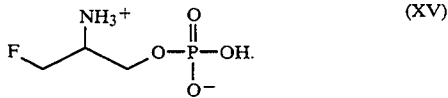

All of the references cited herein are hereby incorporated in their entireties by reference.

While this invention has been described with an emphasis upon a preferred embodiment, it will be obvious to those of ordinary skill in the art that variations of the preferred products and methods may be used and that it is intended that the invention may be practiced otherwise than as specifically described herein. Accordingly, this invention includes all modifications encompassed within the spirit and scope of the invention as defined by the following claims.

What is claimed is:

1. A method for preparing sphingosine-1-phosphate of formula III

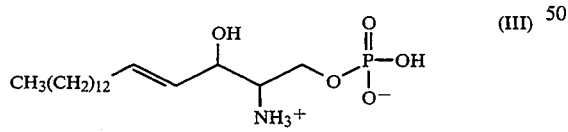

comprising (a) reacting the amine functionality of sphingosine of formula IV

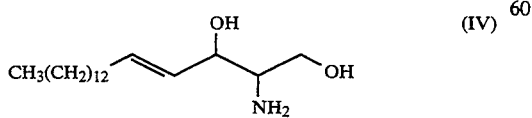

with a compound which comprises amine-blocking group Z to form an amino-blocked sphingosine of formula V

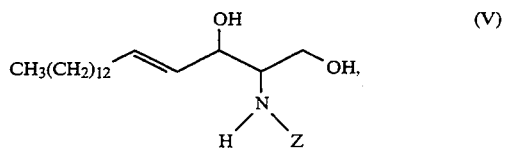

wherein the secondary hydroxyl functionality of the amino-blocked sphingosine is not blocked, (b) reacting the amino-blocked sphingosine of formula V with bis(2-cyanoethoxy)(diisopropylamino)phosphine and oxidizing the resulting compound to form a phosphate triester of formula VI,

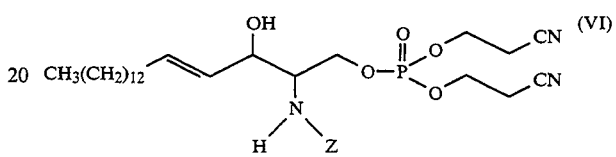

and (c) removing the cyanoethoxy groups and the amine-blocking group Z from the phosphate triester to form sphingosine-1-phosphate.

2. The method according to claim 1, wherein the compound which comprises amine-blocking group Z is di-tert-butyl dicarbonate.

3. The method according to claim 2, wherein the cyanoethoxy groups are removed from the phosphate triester by reacting the phosphate triester with dimethylamine.

4. The method according to claim 3, wherein the blocking group Z on the amine functionality of the phosphate triester is removed by reacting the phosphate triester with trifluoroacetic acid.

5. The method according to claim 4, wherein the oxidation which provides the phosphate triester is completed using iodine.

6. A method for preparing a 1-phosphate derivative of a compound which includes a 2-amino-1,3-alcohol radical comprising (a) reacting each nitrogen of the compound of formula VII

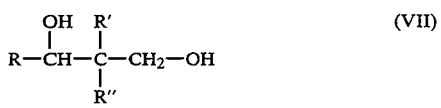

with a compound comprising an amine-blocking group to form an amine-blocked compound, wherein the 3-alcohol functionality is not blocked, (b) reacting the amine-blocked compound formed in step (a) with bis(2-cyanoethoxy)(diisopropylamino)phosphine, (c) oxidizing the compound formed in step (b) to form a phosphate triester, and (d) removing the cyanoethoxy groups and each amine-blocking group from the compound formed in step (c) to form the 1phosphate derivative of formula I

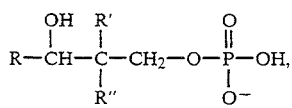

wherein R is a radical containing 1 to 15 carbon atoms, a halogen, or hydrogen, R' is an organic radical or hydrogen, and R" is a radical comprising at least one nitrogen.

7. The method according to claim 6, wherein R is a substituted or unsubstituted alkane or alkene radical.

8. The method according to claim 7, wherein R is a hydrocarbon radical.

9. The method according to claim 8, wherein R' is an organic radical and contains from one or two carbon atoms.

10. The method according to claim 9, wherein R' is a hydrocarbon radical.

11. The method according to claim 9, wherein R in the compound of formula VII is a substituted or unsubstituted alkane hydrocarbon radical.

12. The method according to claim 11, wherein R in the compound of formula I is $CH_3(CH_2)_{14}-$.

13. The method according to claim 12, wherein R' is $-CH=CH_2$ and R" is $-NH_3^+$.

14. The method according to claim 12, wherein R' is H and R" is $-NH-NH_3^+$.

15. The method according to claim 12, wherein R' is $-CH_2F$ and R" is $-NH_3^+$.

16. The method according to claim 12, wherein R' is $-C\equiv CH$ and R" is $-NH_3^+$.

17. The method according to claim 12, wherein R' is $-CH=CHF$ and R" is $-NH_3^+$.

18. The method according to claim 6, wherein the compound which comprises an amine-blocking group is di-tert-butyl dicarbonate.

19. The method according to claim 6, wherein the cyanoethoxy groups are removed by reacting the compound formed in step (c) with dimethylamine.

20. The method according to claim 6, wherein the amine-blocking group is removed by reacting the compound formed in step (c) with trifluoroacetic acid.

* * * * *